United States Patent

Takaoka et al.

Patent Number: 4,987,267
Date of Patent: Jan. 22, 1991

[54] OLIGOHEXAFLUOROPROPYLENE OXIDE COMPOUND TERMINATED WITH VINYL GROUP AT ITS ONE END

[75] Inventors: Akio Takaoka, Takasaki; Noriyuki Koike, Yoshii; Hideki Fujii, Annaka, all of Japan

[73] Assignee: Shin-Etsu Chemical Co., Ltd., Tokyo, Japan

[21] Appl. No.: 463,349

[22] Filed: Jan. 11, 1990

[30] Foreign Application Priority Data

Jan. 12, 1989 [JP] Japan .................................... 1-5594

[51] Int. Cl.$^5$ ............................................. C07C 43/17
[52] U.S. Cl. ...................................... 568/615; 568/685
[58] Field of Search ........................ 568/615, 685, 674

[56] References Cited

U.S. PATENT DOCUMENTS 3,574,770 4/1971 Paine .................................... 568/615

Primary Examiner—Howard T. Mars
Assistant Examiner—Margaret Argo
Attorney, Agent, or Firm—Oblon, Spivak, McClelland, Maier & Neustadt

[57] ABSTRACT

An oligohexafluoropropylene oxide compound having the general formula (I):

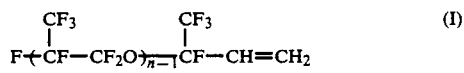

wherein n represents an integer of 2 to 5. The compound is useful for preparing a polymer having good thermal resistance, chemical stability, non-adhesion properties, water and oil repellencies, and flexibility, when copolymerized if other monomers.

1 Claim, 3 Drawing Sheets

OLIGOHEXAFLUOROPROPYLENE OXIDE COMPOUND TERMINATED WITH VINYL GROUP AT ITS ONE END

BACKGROUND OF THE INVENTION

1. Field of the Invention

This invention relates to a novel oligohexafluoropropylene oxide compound terminated with a vinyl group at its one end.

2. Description of the Prior Art

Heretofore, as a linear perfluoro organic compound terminated with a vinyl group at its one end, a perfluoroalkylethylene having the formula:

$$RfCH=CH_2$$

wherein Rf represents a perfluoroalkyl group, is known (French Certificate of Addn. 93 170; French Patent No. 1 560 544). This compound is also known to be readily prepared in the following way: First, as shown by the following reaction equation:

$$RfI + CH_2=CH_2 \rightarrow RfCH_2CH_2I$$

wherein Rf is as defined above, a perfluoroiodoalkane (RfI) obtained by industrial telomerization of tetrafluoroethylene is subjected to addition reaction with ethylene in the presence of azobisisobutylonitrile (AIBN) at a temperature of from 70° to 80° C. to give a 1-perfluoroalkyl-2-iodoethane (see Japanese patent Publication (KOKOKU) No. 21086/1969, U.S. Pat. No. 3,285,393, and West German Patent No. 1 816 706). Next, as shown by the following reaction equation:

$$RfCH_2CH_2I \rightarrow RfCH=CH_2 + HI,$$

the 1-perfluoralkyl-2-iodoethane obtained as above is subjected to dehydroiodination in the presence of a base (Japanese patent publication (KOKOKU) No. 26601/1989).

However, the compound this invention provides, terminated with a vinyl group at its one end and wherein the linear perfluoro chain moiety is composed of a perfluoroether chain is unknown in the art.

SUMMARY OF THE INVENTION

An object of this invention is to provide an oligohexafluoropropylene oxide terminated with a vinyl group at its one end, which is useful as an intermediate for synthesizing various compounds.

This invention provides an oligohexafluoropropylene oxide compound having the general formula (I):

$$F\mathord{-}(\underset{\underset{CF_3}{|}}{CF}-CF_2O)_{\overline{n-1}}\underset{\underset{CF_3}{|}}{CF}-CH=CH_2 \quad (I)$$

wherein n represents an integer of 2 to 5.

This compound is useful as an intermediate for synthesizing various compounds. For example, copolymerization thereof with a fluoroolefin can give a polymer having excellent thermal resistance, chemical stability, non-adhesion properties, water repellency, oil repellency, and flexibility, and also capable of being melt-molded. Thus, it is useful in the fields of resins and elastomers. A hybrid silicone containing this compound as a monomer unit is expected to be applicable as an elastomer with a low surface energy, having good thermal resistance and low-temperature properties, and also having water repellency, oil repellency and stain resistance properties.

DETAILED DESCRIPTION OF THE PREFERRED EMBODIMENTS

Figure 1:
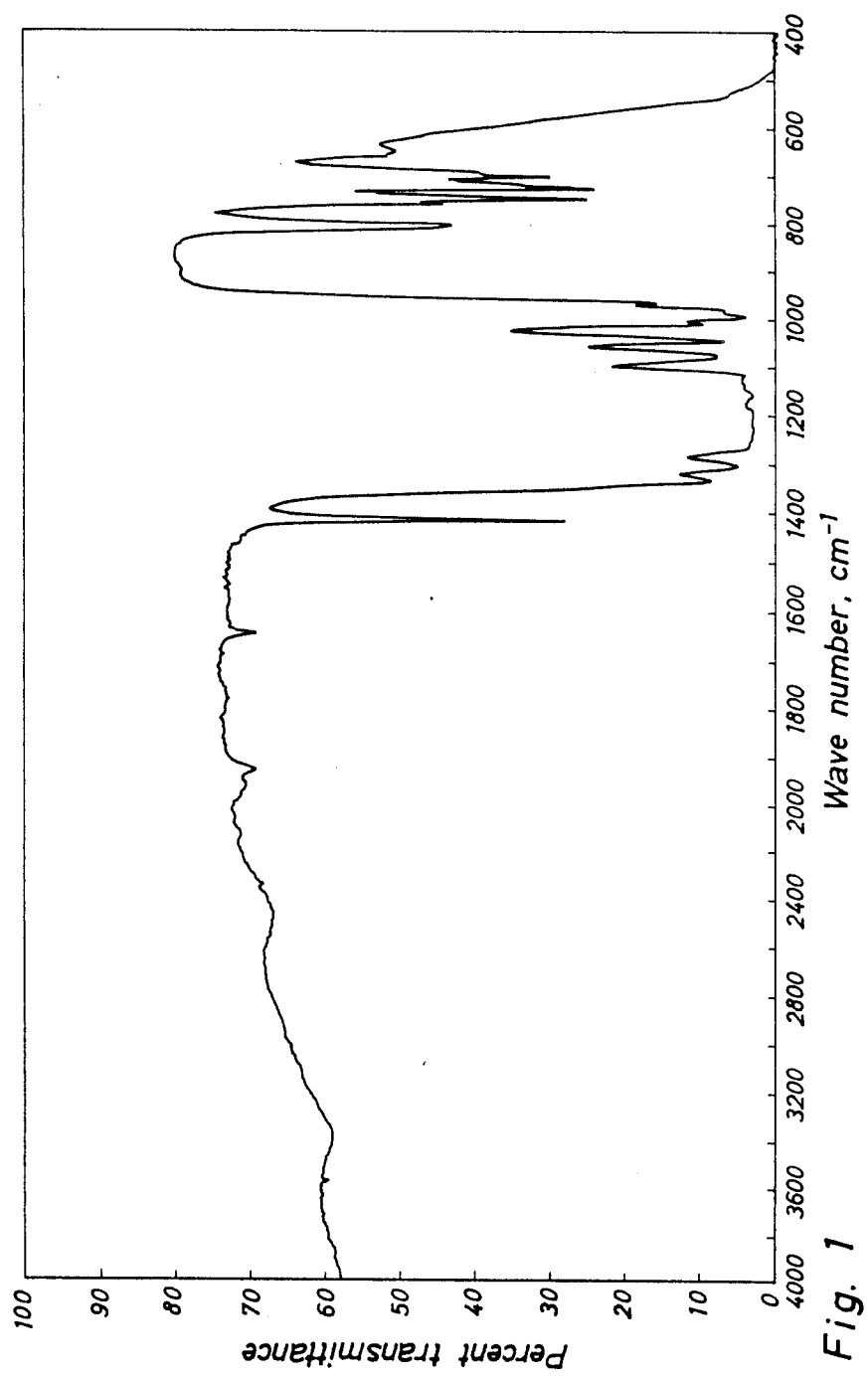
FIGS. 1 to 3 show infrared spectra of the compounds of this invention obtained in Examples 1 to 3, respectively.

The oligohexafluoropropylene oxide compound having the above general formula (I) can be prepared, for example, by subjecting a secondary alcohol having the following general formula (II):

$$F\mathord{-}(\underset{\underset{CF_3}{|}}{CFCF_2O})_{\overline{n-1}}\underset{\underset{OH}{|}}{\underset{\underset{CF_3}{|}}{CF}CHCH_3} \quad (II)$$

to dehydration using a dehydrating agent. This dehydration can be achieved by heating the secondary alcohol of the general formula (II) up to about 360° C. in the presence of the dehydrating agent, for example, phosphorus pentoxide ($P_2O_5$) [see J. Am. Chem. Soc., 75, 5618 (1953)].

The secondary alcohol of the general formula (II), used as the starting material in the above reaction can be prepared from hexafluoropropylene oxide (HFPO) by known methods in the following way.

First, as shown by the following equation:

$$CF_3CF\mathord{-}\!\!\!\diagdown\!\!\!\diagup\!\!\!\mathord{-}CF_2 \longrightarrow \quad (III)$$
$$\underset{O}{}$$
$$F\mathord{-}(\underset{\underset{CF_3}{|}}{CFCF_2O})_{\overline{n-1}}\underset{\underset{CF_3}{|}}{CF}COF,$$

HFPO is added into, for example, a cesium fluoride/tetraglyme system to synthesize an acyl fluoride of an n-mer (n=2 to 5) of HFPO, and the resulting acyl fluoride is separated by distillation.

Next as shown by the equation (IV):

$$F\mathord{-}(\underset{\underset{CF_3}{|}}{CFCF_2O})_{\overline{n-1}}\underset{\underset{CF_3}{|}}{CF}COF + CH_3OH \longrightarrow \quad (IV)$$
$$F\mathord{-}(\underset{\underset{CF_3}{|}}{CFCF_2O})_{\overline{n-1}}\underset{\underset{CF_3}{|}}{CF}CO_2CH_3,$$

the acyl fluoride is esterified with methanol.

Then, as shown in the following equation (V):

$$F\mathord{-}(\underset{\underset{CF_3}{|}}{CFCF_2O})_{\overline{n-1}}\underset{\underset{CF_3}{|}}{CF}CO_2Me \xrightarrow{MeMgI + i\text{-}PrMgBr/Et_2O} \quad (V)$$
$$F\mathord{-}(\underset{\underset{CF_3}{|}}{CFCF_2O})_{\overline{n-1}}\underset{\underset{OH}{|}}{\underset{\underset{CF_3}{|}}{CF}CHCH_3}$$

wherein Me represents the methyl group; i-Pr, the isopropyl group; and Et, the ethyl group, the methoxycarbonyl group of the ester obtained in the above is converted into a methyl carbinol to give the secondary polyfluoroalcohol of the above general formula (II). This reaction can be carried out by known methods see J. Am. Chem. Soc., 75, 6324 (1953) and J. Fluorine Chem., 1, 203 (1971)]. More specifically, the ester is allowed to react with the Grignard reagent (MeMgI+i-PrMgBr) in the presence of diethyl ether. Here, the reaction is carried out at a temperature of from 0° to 5° C. for about 1 to 5 hours at the initial stage, and thereafter at a temperature of from 10° to 30° C. for about 10 to 30 hours.

The compound of this invention is hardly homopolymerizable as a monomer, but is copolymerizable or terpolymerizable with, for example, fluoroolefins including tetrafluoroethylene, or perfluoroalkyl vinyl ethers, and is useful as an intermediate for synthesizing various compounds. The copolymers or terpolymers thus prepared have excellent thermal resistance, chemical stability, non-adhesion properties, water repellency, oil repellency, and flexibility, and are also capable of being readily melt-molded. Moreover, hybrid fluorosilicones obtained by hydrosilylation of the compound of this invention with an organosilane or organopolysiloxane having an Si—H bond can also have good thermal resistance and low-temperature properties, and also have water and oil repellencies, high stain resistance, and low surface energy, thus promising its great utility.

EXAMPLES

This invention will be described below in greater detail by giving working examples.

EXAMPLE 1

A flask of 0.5 lit. in internal volume was equipped with a mechanical stirrer, on which a distillation unit was mounted. A receptacle for fractions was cooled with a dry-ice condenser. In this flask, 611 g of a secondary alcohol (purity: 95%; 1.17 mols) having the following formula (VI):

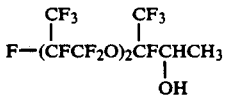

(VI)

and 170 g (1.20 mols) of phosphorus pentoxide were charged. While the contents of the flask were thoroughly stirred with the stirrer, they were slowly heated with a mantle heater, and the temperature was controlled so that the distillation rate was made constant. During this operation, the temperature of the mantle heater was measured using a thermocouple, and it was raised up to about 360° C., at which little distillate was produced; hence the heating was stopped.

The resulting distillate was washed with saturated sodium carbonate and subsequently with saturated brine, followed by addition of magnesium sulfate and drying. Next, the distillation was again carried out to give 467 g of a product as a fraction having boiling points of from 132° to 133° C. (yield: 82%).

The compound thus obtained was subjected to elementary analysis, analysis by GC/MS, and measurement for both infrared spectrum and ¹H-NMR spectrum. Results obtained are shown below.

| | Elementary analysis | | |
|---|---|---|---|
| | C | H | F |
| Calculated*: (%) | 25.12 | 0.63 | 67.55 |
| Found: (%) | 25.01 | 0.58 | 67.61 |

*Calculated as $C_{10}F_{17}H_3O_2$.

GC/MS

Molecular weight: 478 (M-19: 459)

Infrared spectrum

FIG. 1 shows the infrared spectrum. As will be evident therefrom, the absorption at 3,420 cm⁻¹ due to —OH has disappeared and another absorption due to C=C is seen to have appeared at 1,660 cm⁻¹.

¹H-NMR

Carbon tetrachloride and tetramethylsilane were used as a solvent and an internal standard, respectively.
δ(ppm): 6.0 (m, 1H, CH) 5.83 (m, 2H, CH₂=)

From the foregoing results, the product was identified to be the compound having the following formula:

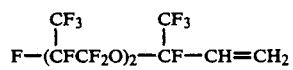

EXAMPLE 2

The procedure of Example 1 was repeated except that the secondary alcohol of the formula (VI) as used in Example 1 was replaced with 330 g (1.0 mol) of a secondary alcohol having the following formula:

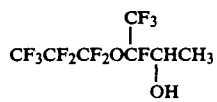

to give 243 g of a product having a boiling point of 77.5° to 78° C. (yield: 78%). This product was subjected to analyses and measurement in the same manner as in Example 1. As a result, the following results were obtained.

| | Elementary analysis | | |
|---|---|---|---|
| | C | H | F |
| Calculated*: (%) | 26.94 | 0.97 | 66.96 |
| Found: (%) | 26.81 | 0.95 | 67.02 |

*Calculated as $C_7F_{11}H_3O$.

GC/MS m/e (M+) Molecular weight: 312

Infrared spectrum

Figure 2:
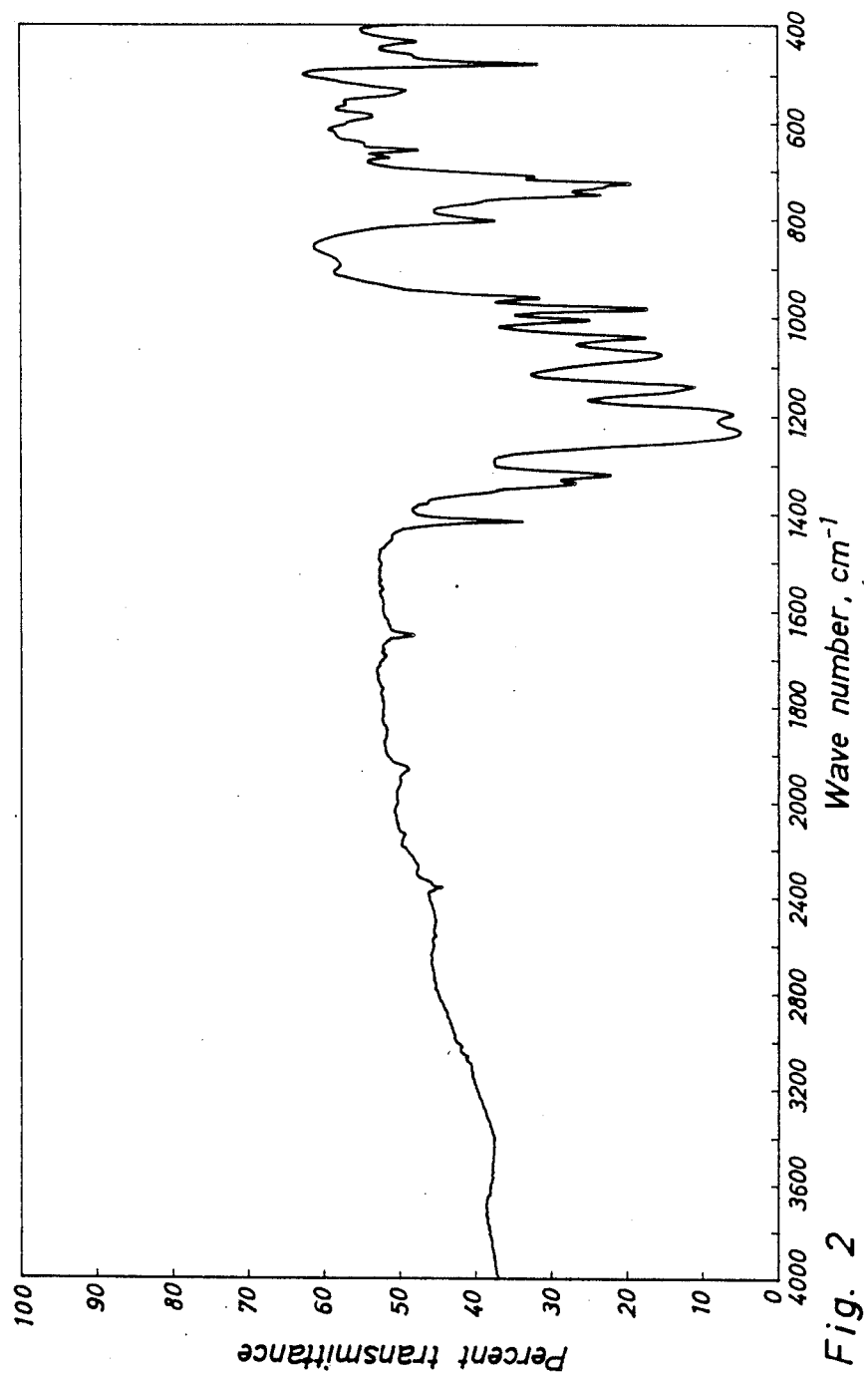

As shown in FIG. 2. As will be evident therefrom, the absorption at 3,420 cm⁻¹ due to —OH has disappeared and another absorption due to C=C is seen to have appeared at 1,650 cm⁻¹.

¹H-NMR

Carbon tetrachloride and tetramethylsilane were used as a solvent and an internal standard, respectively.

δ(ppm): 5.63 to 5.89 (m, 1H, —CH=) 5.34 to 5.63 (m, 2H, =CH₂)

From the foregoing results, the product was identified to be the compound having the following formula:

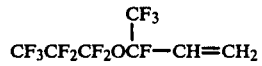

EXAMPLE 3

The procedure of Example 1 was repeated except that the secondary alcohol of the formula (VI) as used in Example 1 was replaced with 662 g (1.0 mol) of a secondary alcohol having the following formula:

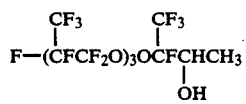

to give 580 g of a product having a boiling point of from 78° to 79° C./20 mmHg (yield: 90%). This product was subjected to analyses and measurement in the same manner as in Example 1. As a result, the following results were obtained.

| | Elementary analysis | | |
|---|---|---|---|
| | C | H | F |
| Calculated*: (%) | 25.12 | 0.63 | 67.55 |
| Found: (%) | 25.01 | 0.58 | 67.61 |

*Calculated as $C_{10}F_{17}H_3O_2$.

GC/MS m/e (M⁺) Molecular weight: 644

Infrared spectrum

Figure 3:
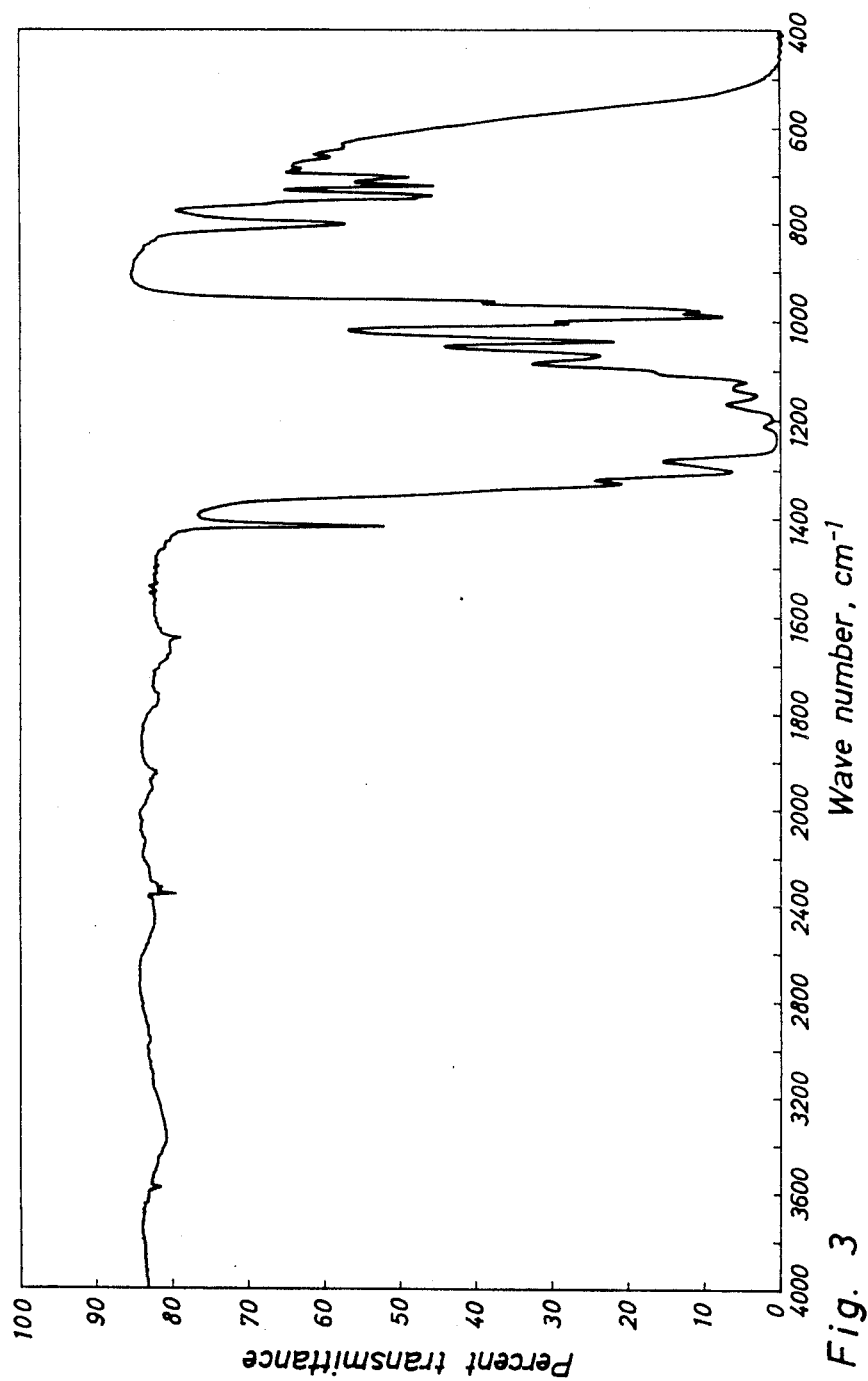

As shown in FIG. 3. As will be evident therefrom, the absorption at 3,420 cm⁻¹ due to —OH has disappeared and another absorption due to C=C is seen to have appeared at 1,650 cm⁻¹.

¹H-NMR

Carbon tetrachloride and tetramethylsilane were used as a solvent and an internal standard, respectively.

δ(ppm): 5.77 to 6.13 (m, 1H, —CH=) 5.43 to 5.77 (m, 2H, =CH₂)

From the foregoing results, the product was identified to be the compound having the following formula:

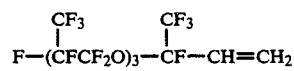

We claim:
1. A compound of the formula:

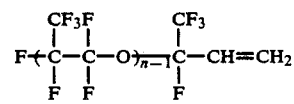

wherein n is an integer of 2 to 5.